United States Patent
Traneus et al.

(10) Patent No.: US 11,389,669 B2
(45) Date of Patent: Jul. 19, 2022

(54) SYSTEM AND METHOD FOR RADIOTHERAPY TREATMENT PLANNING AND DELIVERY

(71) Applicant: RaySearch Laboratories AB, Stockholm (SE)

(72) Inventors: Erik Traneus, Uppsala (SE); Kjell Eriksson, Bålsta (SE); Erik Engwall, Hägersten (SE); Rasmus Bokrantz, Stockholm (SE); Albin Fredriksson, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 17/044,497

(22) PCT Filed: Apr. 1, 2019

(86) PCT No.: PCT/EP2019/058156
§ 371 (c)(1),
(2) Date: Oct. 1, 2020

(87) PCT Pub. No.: WO2019/192951
PCT Pub. Date: Oct. 10, 2019

(65) Prior Publication Data
US 2021/0038914 A1 Feb. 11, 2021

(30) Foreign Application Priority Data
Apr. 3, 2018 (EP) .................................. 18165472

(51) Int. Cl.
*A61N 5/10* (2006.01)
*G16H 20/40* (2018.01)

(52) U.S. Cl.
CPC ......... *A61N 5/1031* (2013.01); *A61N 5/1081* (2013.01); *G16H 20/40* (2018.01)

(58) Field of Classification Search
CPC .................... A61B 5/128; A61F 11/00; A61M 2021/0027; A61N 1/36036; A61N 1/361; H04R 25/75
See application file for complete search history.

(56) References Cited

U.S. PATENT DOCUMENTS

| 2015/0217135 A1* | 8/2015 | Bohsung | A61N 5/103 250/492.3 |
| 2017/0036043 A1* | 2/2017 | Dilmanian | A61N 5/1084 |
| 2017/0281980 A1* | 10/2017 | Wulff | H01J 37/08 |

FOREIGN PATENT DOCUMENTS

| WO | WO-2017/082984 A1 | 5/2017 | |
| WO | WO-2017/156419 A1 | 9/2017 | |
| WO | WO-2017156419 A1 * | 9/2017 | ........... A61N 5/1065 |

OTHER PUBLICATIONS

Ding, Xuanfeng et al., "Spot-Scanning Proton Arc (SPArc) Therapy: The First Robust and Delivery-Efficient Spot-Scanning Proton Arc Therapy," Int J Radiation Oncol Biol Phys, vol. 96, No. 5, pp. 1107-1116, 2016.

(Continued)

*Primary Examiner* — Christine H Matthews
*Assistant Examiner* — Joshua Daryl D Lannu
(74) *Attorney, Agent, or Firm* — Faegre Drinker Biddle & Reath LLP

(57) ABSTRACT

A method of radiotherapy treatment planning for creating a plan for delivery of radiation to a patient in at least one particle-based arc is proposed. The delivery time for the plan is reduced by including a penalty in the objective function, designed to limit the number of energy layers and/or the number of energy layer changes.

10 Claims, 2 Drawing Sheets

(56) References Cited

OTHER PUBLICATIONS

Van De Water, Steven, et al., "Shortening Delivery Times of Intensity Modulated Proton Therapy by Reducing Proton Energy Layers During Treatment Plan Optimization," International Journal of Radiation Oncology Biology Physics, vol. 92, No. 2, pp. 460-468, Jun. 1, 2015.

* cited by examiner

SYSTEM AND METHOD FOR RADIOTHERAPY TREATMENT PLANNING AND DELIVERY

This application is the National Stage of International Application No. PCT/EP2019/058156, filed Apr. 1, 2019, and claims benefit of European Patent Application No. 18165472.4, filed Apr. 3, 2018, the entire contents of which are incorporated by reference herein.

TECHNICAL FIELD

The present invention relates to a system and a method for particle-based radiotherapy treatment planning and delivery.

BACKGROUND

In particle-based radiotherapy treatment, patients are irradiated with Charged particles such as protons. The particles are controlled in such a way that they will deposit most of their energy at specific depths in the patient so that the whole target will be covered. At the same time, some energy will be deposited along the path towards the target. Each particle will deposit most of its energy towards the end of its path, in what is known as the Bragg peak. The depth of the Bragg peak in the patient can be controlled by adjusting the kinetic energy of the particles. The lateral position of the Bragg peak can be controlled using electromagnets to deflect the focused beam. This allows for the delivery of highly localized doses at well-controlled positions in the patient. The dose delivered from a certain combination of kinetic energy, and lateral deflection of the beam is referred to as a spot. The number of particles delivered to a spot is commonly referred to as the spot weight. By providing spots in many different locations in a three-dimensional space, the target volume can be fully covered with the desired dose distribution. This procedure is called active scanning ion beam therapy, also known as pencil beam scanning.

The kinetic energies of the spots are often, but not necessarily, distributed over a number of discrete energies. A group of spots with the same kinetic energy, but different lateral deflection is often referred to as an energy layer. To cover a desired volume in a patient, different energy layers are defined such that particles of a particular energy layer will deposit their energy at a certain depth in the patient. The energy layers are selected in such a way that the Bragg peaks will be distributed over the volume to be treated.

The spot weights of each energy layer are determined in the treatment planning system through optimization, and the spot weights are iteratively varied to achieve desired objectives or constraints related to dose levels or other relevant quantities. The case where the spot weights are allowed to vary freely over the beams is referred to as intensity modulated proton therapy (IMPT).

In photon-based radiotherapy it is more difficult to control exactly where the photons will deposit their energy. Therefore, it is common to irradiate the patient using a high number of beams from different angles. In this way, all beams will deposit dose in the target while the dose deposited to any intermediate tissue will be limited. Typically, a radiotherapy treatment apparatus comprises a gantry that is able to rotate around the patient to irradiate from different angles, or even continuously during movement. Such treatment methods, in which a patient is irradiated by a plurality of beams from different directions, are referred to as arc therapy, or multi-arc therapy. In proton treatment the use of arc therapy has been proposed, but is not yet clinically used.

Proton arc therapy involves radiation in a sequence of a large number of beams from different angles, for example 10 or more, 50 or more, or 100 or more angles, each having a number of energy layers, for example up to 20 energy layers. The adjustment between each energy layer, and between each angle, takes time. The arc can be delivered either as multiple separate beams or through a continuous moving arc. In the latter case, the beams will serve as control points as we know it from photon arc therapy. Hereinafter, the terms beam, beam direction or beam angle could equally well be substituted by the term control point, if the arc is continuous. There is always a desire to reduce delivery time, while still maintaining a high quality plan which will ensure effective treatment of the patient.

Beaumont, Xuanfeng Ding et al, Int J Radiation Oncol Biol Phys, Vol. 96, No. 5, pp. 1107e1116, 2016) propose an iterative method for proton arc therapy including, in each iteration, control point resampling, energy layer redistribution, energy layer filtration, and energy layer resampling. Each control point corresponds to a beam. A small number of control points are defined, each with a number of energy layers, and the plan is optimized. The control points are then split by replacing one original control point with a pair of adjacent sub-control points and the energy layers of the original control point are split between the sub-control points, before optimizing the plan again. Spots having a low weight may be filtered out. This may be repeated a number of times.

In photon based radiotherapy and in passively scattered proton radiotherapy, the fluence irradiated from each angle is limited by the use of collimators. To avoid manufacturing beam specific apertures for each angle, adaptive apertures are often used in photon treatments. The use of adaptive apertures has been proposed in proton therapy but is not common practice. In active proton treatments, the protons are actively steered to cover the target and no aperture is needed to limit the initial fluence. However, the lateral edge of each beam will be more or less sharp, depending on the apparatus, but there will always be a blurred area at the lateral edge, which is known as a penumbra. To obtain a sharper edge, an aperture could be used. Apertures in proton treatment are normally patient and beam specific and are costly to manufacture. In arc therapy, use of beam-specific apertures would mean manufacturing a large number of apertures and would also mean changing the aperture for each beam within an arc, which would be both expensive and prohibitively time consuming.

SUMMARY

It is an object of the present invention to provide a high-quality treatment particle-based arc radiotherapy treatment plan with a shortened delivery time.

The invention proposes methods for planning particle-based radiotherapy treatment, as well as computer program products and an apparatus for delivering such treatment. In particular, the inventive method proposes a method of reducing the number of energy layers used in the plan while maintaining plan quality.

The invention relates to a method of radiotherapy treatment planning for creating a plan for delivery of at least one particle-based arc to a patient using an apparatus arranged to deliver radiation in the form of charged particles from a number of different directions comprising the steps of a. determining at least one arc trajectory including a set of beam angles b. determining a set of energy layers for each beam angle c. optimizing the plan using an optimization problem formulation designed to produce a suitable dose distribution, in such a way that the plan will use only subsets of beam angles and energy layers from the set of beam angles and the set of energy layers, respectively, wherein the optimization is subject to a penalty designed to limit the number of energy layers.

The method and system according to the invention enables optimization of a particle-based arc therapy treatment plan resulting in a low number of energy layers, while still ensuring plan quality. This can be achieved according to the invention by one single optimization. It would also be possible to perform the optimization iteratively, although this would take more time.

The therapy treatment plan may involve the delivery of radiation in the form of charged particles from a number of different directions, either by arc or by multiple beams. The penalty may be defined as a constraint or a term in an objective function used in the optimization.

The penalty may be expressed in terms of the number of energy layers. Minimizing the number of energy layers used reduces the plan delivery time because changing between different energy layers is time consuming. Alternatively, the penalty may be expressed in terms of the number of energy layer changes between adjacent angles. This will enable, for example, keeping the energy layer when changing beam angles, thus saving time. It is also possible to express the penalty in terms of both the number of energy layers and the number of energy layer changes.

The penalty may be defined to act on the entire arc or on one or more sub-sets of the arc, each sub-set comprising one or more beams.

To further improve the optimization, a robust optimization method may be used to account for uncertainties that may occur during delivery of the plan.

According to preferred embodiments, the method also comprises the step of applying a ripple filter in the beam trajectory and controlling the ripple filter to spread the Bragg peak of the particles in a suitable way to enable the further reduction of energy layers needed to create a robust plan. The spreading of the Bragg peak serves to broaden each energy layer, thereby further reducing the number of energy layers needed.

The invention also relates to a computer program product for controlling a radiotherapy planning apparatus, preferably stored on a carrier such as a non-transitory storage means, said computer program product comprising computer readable code means which when run in a processor of a radiotherapy planning apparatus will cause the apparatus to perform the method as discussed above.

The invention also relates to a radiotherapy treatment planning apparatus comprising a processor and a program memory holding a computer program product according to the above, arranged to be run in the processor to control the radiotherapy treatment planning apparatus.

According to preferred embodiments, the method also comprises the step of defining and applying an aperture specific for each beam or energy layer to limit each beam or energy layer to its appropriate cross-section. This serves to sharpen the lateral penumbra of each beam.

In some embodiments, an adaptive aperture is used to limit the penumbra for each beam direction. An adaptive aperture for a particle therapy system is disclosed in WO 2017/082984, which describes a system available from Mevion. While this aperture could be used in the method and apparatus according to the invention, such use is not foreseen in the prior art. Of course, any available adaptive aperture suitable for radiotherapy treatment using charged particles could be used in the context of the invention. It could for example be of the type conventionally used for photon based radiotherapy, i.e. a multi-leaf collimator (MLC), but adapted for ion therapy.

BRIEF DESCRIPTION OF THE DRAWINGS

The invention will be described in more detail in the following, by way of example and with reference to the appended drawings, in which.

DETAILED DESCRIPTION

Figure 1:
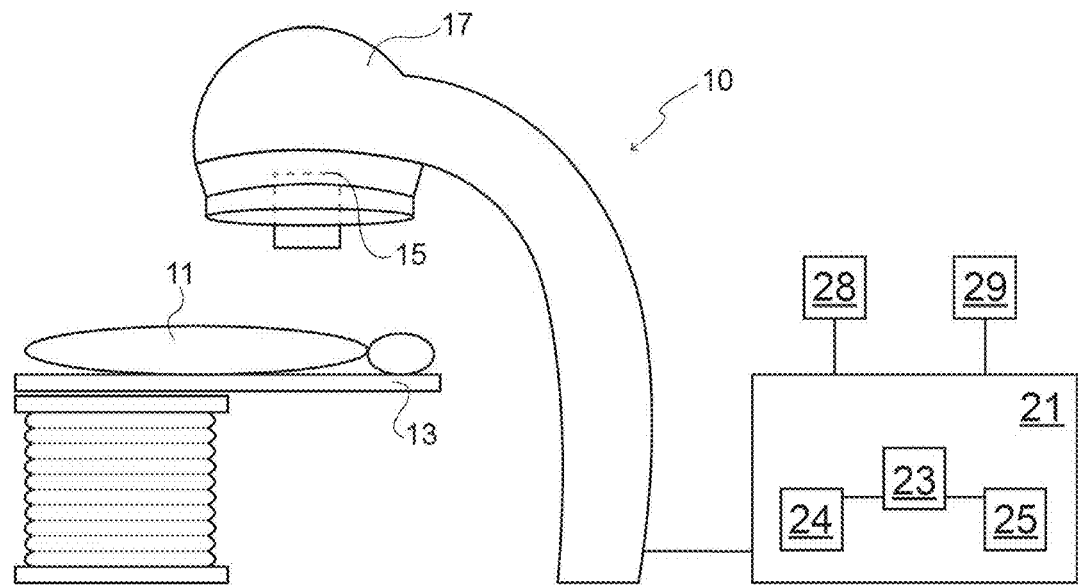
FIG. 1 shows a radiotherapy treatment system in which the invention may be applied

FIG. 1 is an overview of a system for radiotherapy treatment imaging and/or planning. As will be understood, such systems may be designed in any suitable way and the design shown in FIG. 1 is only an example. A patient 11 is positioned on a treatment couch 13. The system comprises a treatment unit 10 having a radiation source 15 mounted in a gantry 17 for emitting radiation towards the patient positioned on the couch 13. Typically, the couch 13 and the gantry 17 are movable in several dimensions relative to each other, to provide radiation to the patient as flexibly and correctly as possible. In particular, the gantry can rotate around the couch, either between certain angles or a full 360° rotation. Alternatively, the gantry can be fixed and the couch carrying the patient can rotate instead. Another alternative is to have the patient in seated position in a chair. The arc treatment in this case could be performed by changing the beam directions or rotating the chair. These parts are well known to the skilled person. The system also comprises a computer 21 which may be used for radiotherapy treatment planning and/or for controlling radiotherapy treatment. As will be understood, the computer 21 may be a separate unit not connected to the imaging unit.

The computer 21 comprises a processor 23, a data memory 24, and a program memory 26. Preferably, one or more user input means 28, 29 are also present, in the form of a keyboard, a mouse, a joystick, voice recognition means or any other available user input means. The user input means may also be arranged to receive data from an external memory unit.

The data memory 24 comprises clinical data and/or other information used to obtain a treatment plan, including a set of clinical goals to be used for planning. The data memory 24 also comprises one or more dose maps for one or more patients to be used in treatment planning according to embodiments of the invention. The program memory 26 holds a computer program, known per se, arranged for treatment plan optimization. The program memory 26 also holds a computer program arranged to make the computer control the treatment of a patient in accordance with the invention.

As will be understood, the data memory 24 and the program memory 26 are shown and discussed only schematically. There may be several data memory units, each holding one or more different types of data, or one data memory holding all data in a suitably structured way, and the same holds for the program memories. One or more memories may also be stored on other computers. For example, the computer may only be arranged to perform one of the methods, there being another computer for performing the optimization.

Figure 2:
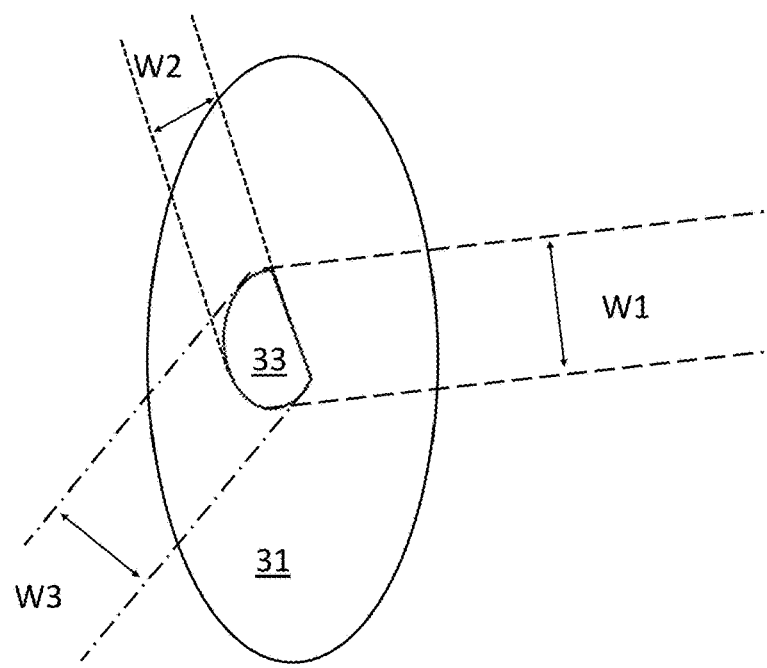
FIG. 2 illustrates a simplified section through a patient receiving arc treatment

FIG. 2 is a simplified view of a patient 31 having a tumour 33 that is to be irradiated. Three different beams are shown each reaching the tumour from a different angle, a first beam illustrated by dashed lines, a second beam illustrated by dotted lines and a third beam illustrated by dash-dotted lines. The number of beams is limited to three for clarity only. As explained above, conventional multi-arc treatment involves a high number of beams in a sequence for a single treatment, typically more than 10, each beam having a number of energy layers. The invention aims at reducing the number of beams in the sequence and/or the number of energy layers, while maintaining plan quality.

As can be seen in FIG. 2, the cross-section of the tumour is very different seen from different angles, the width W1 of the first beam being clearly greater in this example than the width W2 of the second beam. Hence, if apertures are to be used, different shapes of the apertures are preferably used to adapt each of the different beams to the relevant cross-sectional area. This may be achieved by using a dynamically adaptive aperture.

Figure 3:
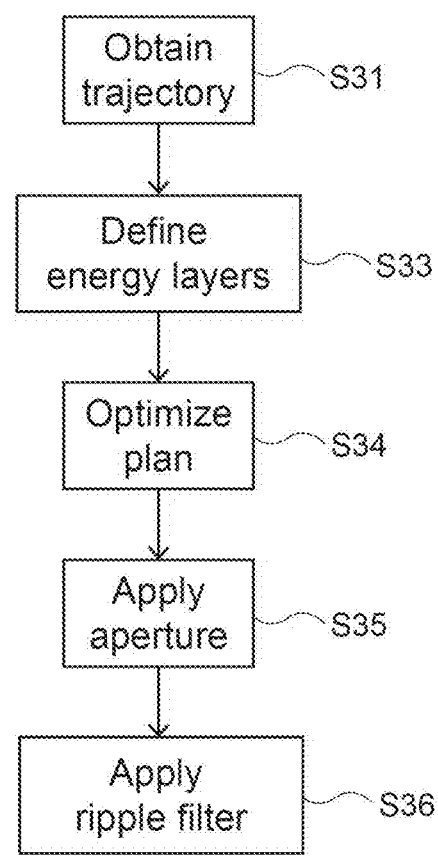
FIG. 3 is a flow chart of a possible method according to the invention

FIG. 3 is a flow chart of an embodiment of the inventive method.

In step S31 an arc trajectory is obtained in any suitable way. The arc defines the angular area in which beam directions may be arranged, and the direction for each beam. This may be done in different ways, including
 a. retrieving a pre-defined trajectory
 b. user-defining a trajectory
 c. automatically creating a situation-specific arc trajectory based on the patient geometry, while taking into account machine limitations such as gantry and couch limitations and potential collisions with the patient.

The trajectory that is retrieved, defined or created in step S31 is typically defined by start and stop angles and a set of beam angles within the arc trajectory. Instead of defining discrete beam angles, a continuous beam could be used. The different beam angles can be achieved through rotation of the gantry and/or the treatment couch or chair and/or the collimator. The method could also include translation of the gantry or couch or chair.

In alternative c of step S31, the automatic creation may be achieved by optimizing the trajectory separately based, for example, on the patient geometry. Alternatively, this automatic creation could be part of the plan optimization process. For example, a predefined trajectory could be optimized by using the angles of the trajectory as variables in the plan optimization process, so that they can be used locally. Yet another option would be to start with a large number of possible trajectories and select the best one based on, for example, cardinality constraints, in a similar way to the conventional method of selecting energy layers based on cardinality constraints. The concept of cardinality constraints will be explained below.

In step S33, a set of energy layers for each beam is defined. For pencil beam scanning treatment methods, a set of spots for each layer is also defined. The set of beam directions and energy layers include all possible beam directions and energy layers that may be included in the treatment plan. The set of energy layers for each beam direction could be chosen in any suitable way. For example, they may be chosen based on the physical properties of the patient, for example according to one or more of the following:
 a. the mid-plane of the target in water-equivalent path length (WEPL) space
 b. the distal edge of the target in WERE, space
 c. The full set of energy layers as they would be used in IMPT.

It would also be possible to choose the same set of energy layers for all beam angles, based on which energies are needed to cover different parts of the target in WEPL space from all beam angles. This enables a reduced number of energy layer changes between beam angles because a change of energy layer could always be avoided when changing the beam angle.

If the arc comprises a large number of angles, this could be exploited in the setup of the initial spot pattern in each energy layer to increase the spot spacing, thus reducing the total number of spots, which will result in a lower surface dose.

An alternative to placing the Bragg peaks within the target or in close vicinity to the target, is to use higher energies, so that the Bragg peaks will be placed behind the target in the patient or could even achieve punch through of the patient. The high energy will result in sharper penumbras in the target. As the beam is rotated, the downstream dose outside of the target will be smeared out. In this alternative a single energy layer could be used for all angles to achieve the shortest possible treatment time. In this alternative, the treatment can potentially be achieved with a uniform fluence from each direction. Such a uniform fluence can be achieved with a scanning machine with uniform weights for all spots for a specific direction, or with a scattering system. The optimization is then reduced to vary the weight of the uniform fluence from each direction.

In step S34, the treatment plan is optimized based on the set of beam directions and energy layers defined in steps S31 and 33. In the optimization problem, one or more penalties are set on the number of energy layers, and/or the number of energy layer changes, and/or on the number of beams. In the following, the singular form "penalty" is used, but it should be understood that a number of penalties may be applied together. The penalty may be defined as a constraint, setting an absolute limit, or as terms in the objective function, reflecting a desire to limit the number of energy layers as much as possible. The penalty may be defined in terms of limiting the number of energy layers, of limiting the number of changes of energy layer during the treatment, or in any other suitable way that will ensure that the optimization algorithm will systematically reduce the time that will have to be spent changing between energy layers during treatment delivery.

The optimization may start with the full set of beam angles and energy layers, so that the optimization process will reduce the number of beam angles and energy layers by removing the ones that make the smallest contributions to the plan. Alternatively, the optimization may start with no beam angles and energy layers and the optimization process will proceed to add the ones that make the most useful contributions to the plan. In both cases, the beam angles and energy layers considered are the ones from the sets defined in steps S31 and S33. Some more specific examples of both types of optimization methods will be discussed below.

The penalty may be set to act on the entire arc, limiting the number of energy layers per arc to a maximum value. Alternatively, the penalty may be set to act on each angle individually, to set a maximum number of energy layers per beam. As a third option, sub-arcs, each containing a subset of the arc, could be defined and the penalty may be set to limit the number of energy layers for each sub-arc. The same applies if the penalty is set in terms of an objective function. A sub-arc could comprise any suitable number of consecutive beams, for example, three or five, but a sub-arc could also comprise only one beam.

In particular, if the penalty is specified to limit the number of energy layer changes, it will be suitable to set the penalty to the whole arc or to sub-arcs comprising more than one angle. This is because in this case such a penalty can avoid changing the energy layer between two beams by using the last energy layer in one beam as the first energy layer in the next beam.

The energy layer selection penalty can be formulated mathematically by introduction of a function $y: R^m \to R^n$ that maps vectors of spot weights $x \in R^m$ (defined across all energy layers and angles) to some measure of how much each energy layer at each angle is used. The component functions $y_1, \ldots, y_n$ may preferably be defined such that that $y_i(x)$ is positive if the combination of energy layer and angle at index i has any spot with positive weight, and zero otherwise. One possible formulation of a component function $y_i$ is as a norm $\|x^i\|$ of a sub-vector $x^i$ that is associated with some energy layer and angle. A penalty on the maximum number of energy layers per arc may with this notation be expressed as card(y)≤b, where the cardinality operator card(·) denotes the number of non-zero entries of a vector. Constraints on sub-arcs or individual angles are similarly formulated with respect to sub-vectors of y. The penalties will be referred to in the following as cardinality penalties.

The objective functions and constraints in the optimization problem should be able to optimize on different quantities, most importantly dose and LET-related quantities, such as LET and dose-weighted LET, (The LET (Linear Energy Transfer) could more efficiently be focused inside the target using proton arcs than in normal IMPT, if considered in the optimization.)

An optimization problem with cardinality penalties can be solved by mixed-integer programming methods. Heuristics methods could also be used to calculate approximate solutions for problem instances that are too large to be computationally tractable. Examples of heuristic methods that are applicable to energy layer selection include but are not limited to:

a. Continuous approximation methods: Such methods will start from the complete set of beams and energy layers and remove some during optimization. The cardinality operator is here approximated by a continuous function, which removes the combinatorial aspect of the problem. The resulting approximate problem can be solved by some method for continuous optimization, such as an interior-point method or a sequential quadratic programming method. One possible reformulation of a problem with cardinality penalties into continuous problem is to express the cardinality operator as a sum of step functions s according to $\text{card}(y)=\Sigma_i s(y_i)$, where s evaluates to zero for nonpositive numbers and one otherwise, and then substitute a continuous but approximate step function for the exact function s. Examples of functions that could be used to approximate s are the logistic function or the error function, or simply the positive part function. The method could be applied in steps, so that multiple optimizations are performed and the accuracy of the approximation of the step function is increased between optimizations until the result is acceptable considering the cardinality penalty. If the cardinality penalty is formulated as a constraint, this means that the constraint is fulfilled. If the cardinality penalty is formulated as a term in the objective function, the term is minimized. Greedy or reverse-greedy methods: A greedy method begins with an empty set of selected combinations of energy layers and angles. Combinations of energy layers and angles are then added to this set one by one based on which combination that gives the largest improvement of the current solution. This procedure continues until the cardinality penalty or penalties prevent any further additions. Which energy layer and angle to add at a given iteration may be determined by performing a spot weight optimization for each of the currently unselected combinations, where the unselected combination is added to the current set of selected combinations. The maximum number of iterations in the many spot weight optimization sub-problems that are solved in each major iteration of the greedy method can be set to a small value in the interest of speed. A reverse-greedy method is similar to a greedy method except that the set of selected energy layers and beam angles contains all possible combinations at the start of the optimization. The combination that leads to the smallest degradation of the current solution is then discarded at each iteration until the set of selected energy layers and angles is feasible with respect to all cardinality penalties, that is, that the penalty is fulfilled, or minimized depending on how the penalty is defined.

b. Column generation method: This is a variant of the greedy or reverse-greedy methods where the selection of energy layer and angle to add or remove is determined based on the gradient information, e.g., the magnitude of the gradient of a merit function that takes both the objective function and the constraints into account. Column generation methods have shorter running times than the original greedy methods because gradient calculations are less costly than optimizations.

c. Stochastic methods: A large number of different heuristics based on random changes to the set of selected energy layers and angles could be used to perform the energy layer selection. Examples include but are not limited to simulated annealing methods, random interchange methods, genetic methods, and tabu search methods. In general, a random change to the current set of selected energy layers and angles is retained if it improves the current solution. Changes that lead to a degradation of the current solution could also be retained with some probability to prevent that the current solution gets trapped in a local but not global optimum.

d. Integer rounding methods (spot filtering methods): The cardinality penalties are in this method disregarded during the spot weight optimization. The spot weights for a subset of the spots are then truncated to zero, with the subset selected so that the optimized solution degrades as little as possible while also satisfying the cardinality constraints. The method could be applied in steps, so that multiple optimizations are performed, and a small subset of spots is removed between optimizations until the cardinality constraint is fulfilled or minimized, depending on how it is formulated, as discussed above.

The different heuristics may preferably be combined with each other. For example, it would be feasible to solve the continuous approximation multiple times while applying the integer rounding method between the iterations to filter out spots and/or energy layers. Another possibility is to utilize several different heuristics in parallel and then discard all but the best solution or subset of best solutions.

The spot filtering methods could filter out low-weight spots as is known in the art, but could additionally be used to reduce degeneracy. For example, if there are many Bragg peaks at the same point or very close to each other, some of the spots may be filtered out. Spot filtering methods may also be used to increase plan robustness. For example, Bragg peaks that are placed so that a density or setup error will result in loss of plan quality, for example, Bragg peaks that are adjacent to critical structures, and risk moving into these if errors occur, could be removed. Similarly, Bragg peaks resulting from ions having a path with large variation in WEPT (quantified for example by the std(WEPL)/WEPL index) could be removed, as the dose contributions of these change much when errors, such as setup and range uncertainty errors, occur.

Energy layers of adjacent angles could additionally be merged to be the same set of energy layers (or single energy) over a sequence of angles, by applying one of the following:
 a. optimization objectives aiming at reducing the number of energy switches between adjacent angles,
 b. algorithms in the energy layer filtration step using limits on when energy layers of adjacent angles can be merged.

The end point could be to have one single set of energies (or single energy) for all angles in the arc, or have the same set of energies for a sequence of angles, i.e. in a sub arc. If the total number of energy layers in the set of energy layers is low, the delivery could be made through a number of consecutive single energy arcs.

Step S35 is an optional step in which a beam-specific aperture for each beam is defined to limit each beam to its appropriate cross-section. During treatment of a patient the treatment process is controlled by a program stored in the program memory 26 of the treatment apparatus. In this process, the beam-specific apertures defined in step S35 may be achieved by controlling the aperture of an adaptive aperture such as the one available from Mevion and described in WO 2017/082984. If the aperture is dynamic, a further possible improvement is to adjust the aperture opening for each energy layer. The resulting optimized and improved plan is stored in the data memory 24 of the treatment apparatus.

Step S36 is an optional step in which a ripple filter is applied in the beam trajectory, and controlled to spread the Bragg peak of the particles in a suitable way to enable the further reduction of energy layers needed to create a robust plan. Ripple filters can also be used to achieve a higher dose smearing in risk organs, when the Bragg peaks are intended to be placed behind the target to achieve sharp penumbras.

To reduce the damage to surrounding tissue further, the described optimization method could be combined with an approach where the plan is set up of similar arcs delivered on different treatment fractions delivered on different days. The different arcs include different beam angles, so that the target is covered in the same way, but the way through the patient to the tumour is different for different fractions.

Radiotherapy using charged particles such as protons enables the optimization of highly precise plans. This in turn means that small errors, for example in the setup, can have large consequences for the delivered dose, Therefore, the optimization method used according to the invention should preferably be a robust optimization method. This becomes even more important when the number of energy layers are reduced. The method should be robust with respect to different uncertainties to ensure that plan quality is preserved even when there are uncertainties in the delivery (e.g. range and setup uncertainties). As an alternative to robust optimization methods, a method aiming at creating uniform doses for each angle (compare SFUD (Single Field Uniform Dose) in normal active scanning plan optimization) or for each set of angles (each sub arc) would be suitable. If a low number of energy layers per angle is desired, the most feasible solution is to aim at uniform doses for each sub arc.

The described methods could be employed for all types of active scanning, including spot scanning, raster scanning, and line scanning. Implementation of line scanning in conjunction with proton arc therapy would be beneficial in terms of delivery time. The methods are suitable for planning treatment of humans, but also of small animals, such as mice, for preclinical trials. The described methods work equally well for other light ions than protons, such as helium, carbon and oxygen, as long as the different biological effects of different ion types are accounted for in biological (RBE) models included in the optimization process.

The invention claimed is:

1. A method of radiotherapy treatment planning for creating and applying a plan for delivery of at least one particle-based arc to a patient using an apparatus arranged to deliver radiation using charged particles from a number of different directions comprising the steps of:
 a. determining at least one arc trajectory including a set of beam angles;
 b. determining a set of energy layers for each beam angle;
 c. optimizing the plan using an optimization problem formulation configured to produce a suitable dose distribution, in such a way that the plan will use only a subset of beam angles and a subset of energy layers from the set of beam angles and the set of energy layers, respectively, wherein the optimization is subject to at least one penalty configured to limit a number of the energy layers; and
 d. storing in a data memory the plan which, when applied by the apparatus arranged to deliver radiation, limits each beam angle or each energy layer to an appropriate cross-section based on the stored plan.

2. The method according to claim 1, wherein the at least one penalty is a constraint or a term in an objective function used in the optimization.

3. The method according to claim 1, wherein the at least one penalty is based on of the number of energy layers.

4. The method according to claim 1, wherein the at least one penalty is defined to act on an entire one of the at least one particle-based arc.

5. The method according to claim 1, wherein the at least one penalty is defined to act on one or more sub-sets of one of the at least one particle-based arc, each sub-set comprising one or more beams.

6. The method according to claim 1, wherein the plan is optimized using an optimization method configured to account for uncertainties during delivery.

7. The method according to claim 1, further comprising the steps of applying a ripple filter in the at least one arc trajectory and controlling the ripple filter to spread the Bragg peak of the particles to limit the number of energy layers needed to create a robust plan.

8. A non-transitory computer-readable storage medium storing thereon a computer-readable code for controlling a radiotherapy planning apparatus, said computer readable code which when run in a processor of a radiotherapy planning apparatus causes the apparatus to perform the method according to claim 1.

9. A radiotherapy treatment planning apparatus arranged to deliver a charged particles based arc therapy, the apparatus comprising a processor and a a non-transitory computer readable storage medium storing a computer-readable code according to claim 8, configured to be run in the processor to control the radiotherapy treatment planning apparatus.

10. The method according to claim 1, wherein the penalty is based on a number of energy layer changes between adjacent angles.

\* \* \* \* \*